(12) United States Patent
Pratapagiri

(10) Patent No.: US 8,259,648 B2
(45) Date of Patent: Sep. 4, 2012

(54) ENHANCED COMMUNICATION OF DATA IN WIRELESS CONTROL AREA NETWORKS

(75) Inventor: Kiran Pratapagiri, Bangalore (IN)

(73) Assignee: General Electric Company, Schenectady, NY (US)

( * ) Notice: Subject to any disclaimer, the term of this patent is extended or adjusted under 35 U.S.C. 154(b) by 1236 days.

(21) Appl. No.: 12/016,305

(22) Filed: Jan. 18, 2008

(65) Prior Publication Data

US 2009/0185548 A1    Jul. 23, 2009

(51) Int. Cl.
*H04W 4/00* (2009.01)
(52) U.S. Cl. .................. 370/328; 370/338; 370/346
(58) Field of Classification Search .................. None
See application file for complete search history.

(56) References Cited

U.S. PATENT DOCUMENTS

| | | | |
|---|---|---|---|
| 6,621,796 B1 * | 9/2003 | Miklos | 370/236 |
| 2004/0153007 A1 | 8/2004 | Harris et al. | |
| 2005/0003794 A1 * | 1/2005 | Liu | 455/355 |
| 2006/0198353 A1 * | 9/2006 | Wason et al. | 370/347 |
| 2006/0268760 A1 * | 11/2006 | Fang et al. | 370/328 |
| 2006/0290516 A1 | 12/2006 | Muehlsteff et al. | |
| 2007/0109117 A1 | 5/2007 | Heitzmann et al. | |
| 2007/0115827 A1 | 5/2007 | Boehnke et al. | |
| 2007/0173701 A1 | 7/2007 | Al-Ali | |
| 2008/0151789 A1 * | 6/2008 | Venkatachalam et al. | 370/280 |
| 2010/0039973 A1 * | 2/2010 | Cavalcanti et al. | 370/311 |
| 2010/0135319 A1 * | 6/2010 | Wang et al. | 370/445 |

OTHER PUBLICATIONS

Emil Jovanov et al., "A wireless body area network of intelligent motion sensors for computer assisted physical rehabilitation", Journal of Neuroengineering and Rehabilitation, v.2, 2005, retrieved from the internet URL: http://www.pubmedcentral.nih.gov/articlerender.fcgi?artid=552302.

Chris Otto et al, "System Architecture of a Wireless Body Area Sensor Network for Ubiquitous Health Monitoring", Journal of Mobile Multimedia, vol. 1, No. 4 (2006), pp. 307-326, retrieved from Internet URL:http://www.ece.uah.edu/~milenka/docs/coamej_imm06.pdf.

* cited by examiner

*Primary Examiner* — Faruk Hamza
*Assistant Examiner* — Tito Pham
(74) *Attorney, Agent, or Firm* — Andrus, Sceales, Starke & Sawall, LLP

(57) ABSTRACT

A method for communicating data in a wireless control area network, where the wireless control area network includes one or more sensor nodes configured to facilitate acquisition of patient data and an access coordinator configured to facilitate acquisition of the patient data from the one or more sensor nodes, is presented. The method includes creating a correlation between one or more poll packets from an access coordinator and time of arrival of data at one or more sensor nodes. Systems and computer-readable medium that afford functionality of the type defined by this method is also contemplated in conjunction with the present technique.

21 Claims, 12 Drawing Sheets

ENHANCED COMMUNICATION OF DATA IN WIRELESS CONTROL AREA NETWORKS

BACKGROUND

This disclosure relates generally to transmission of data in a wireless control area network, and more particularly to a design of a transmission protocol configured to enhance communication of data from one or more sensor nodes to an access coordinator in the wireless control area network.

Patient monitoring devices are typically employed to monitor vital signs associated with a patient and present the physiological data in the form of waveforms or parameters. These patient monitors may also be configured to send audio-visual alarms when the vital signs exceed predetermined threshold values. Further, the patient monitors may be connected to a Local Area Network (LAN) to form a patient monitoring network. Also, central stations may be included in such a network setup, where the central stations may be configured to enable simultaneous review and display the physiological data collected from different patient monitors that are positioned at different locations.

More recently, with the advent of patient monitoring systems using wireless technologies, quality of patient care has been dramatically enhanced. Wireless technologies provide the freedom to communicate and exchange data, thereby enhancing the productivity and convenience of clinical workflows. For example, when a patient connected to a patient monitor is moved from a current location, such as a hospital bed, to a different location, such as an operation theater, the connection to the network may be interrupted and the patient data may be lost. Wireless networks provide an uninterrupted remote view of the patient's condition and thus enhance the quality of patient care.

Recent technological advances in integrated circuits (ICs), wireless communications, and physiological sensing allow miniature, lightweight, ultra-low power, intelligent monitoring sensor devices. A number of these sensor nodes may be integrated into a Wireless Body Area Network (WBAN), a new enabling technology for patient monitoring. The WBAN is a collection of body-worn parameter specific sensors nodes, which communicate to a body-worn access coordinator (AC) using wireless technologies, where the access coordinator may be configured to perform a wireless bridging function to communicate data from the sensor nodes to hospital infrastructure. Use of the WBAN allows the patient freedom to move around, without loss of data, thereby allowing continuous monitoring of the patient.

As will be appreciated, in a typical WBAN, the access coordinator controls the operation of the sensor nodes that exist within the WBAN. Using the currently available techniques, the access coordinator polls the sensor nodes in a round-robin fashion according to a predetermined polling sequence. Individual sensor nodes respond whenever polled by the access coordinator. In other words, the access coordinator notifies all the sensor nodes within the WBAN prior to starting a polling cycle, and the individual sensor nodes prepare data, if any, to be transmitted in response to the poll. Subsequently, the access coordinator starts polling the sensor nodes according to a predetermined polling sequence. During the data transfer period of the communication cycle, the transmission channel is occupied heavily by data bursts present in all the sensor nodes. Furthermore, data bursts from all the sensor nodes come more or less at the same time instant, disadvantageously leading to the data bursts in individual nodes to be substantially synchronized. In addition, the nature of this traffic is generally repetitive in nature. Consequently, this synchronized traffic of data poses a challenge in optimally polling the sensor nodes and efficiently handling bandwidth for data transfer, thereby resulting in data transfer delays. Moreover, the entire cycle period depends upon the time the access coordinator takes to process data and issue a command indicative of an end of communication cycle, which is again random in nature. Therefore, use of the presently available techniques results in an unpredictable amount of delay in the communication of data from the sensor nodes to the access coordinator due to the random nature of the data transfer cycle.

It may therefore be desirable to develop a design of a process that may be configured to advantageously overcome the shortcomings of the presently available techniques. More particularly, it may be desirable to enhance data transfer while minimizing data transfer delays. In addition, it may be desirable for delays associated with the sensor nodes to be as deterministic as possible.

BRIEF DESCRIPTION

In accordance with aspects of the present technique, a method for communicating data in a wireless control area network, where the wireless control area network includes one or more sensor nodes configured to facilitate acquisition of patient data and an access coordinator configured to facilitate acquisition of the patient data from the one or more sensor nodes, is presented. The method includes creating a correlation between one or more poll packets from an access coordinator and time of arrival of data at one or more sensor nodes. Computer-readable medium that afford functionality of the type defined by this method is also contemplated in conjunction with the present technique.

In accordance with further aspects of the present technique, a system for communicating data in a wireless control area network is presented. The system includes one or more sensor nodes configured to facilitate acquisition of data, where the one or more sensor nodes include a processing module, and where the processing module is configured to prepare data for transmission from the one or more sensor nodes to an access coordinator in response to a first beacon transmitted from an access coordinator to the one or more sensor nodes, where the first beacon is configured to indicate a start of a new communication cycle, generate a first data frame, where the first data frame is indicative of a sensor node having data to transmit, and where the first data frame is configured to create a correlation between a poll packet arrival time and a data arrival time at the one or more sensor nodes, transmit the first data frame from at least one sensor node to an access coordinator, and communicate data from the one or more sensor nodes to an access coordinator in response to a second beacon. In addition, the system also includes an access coordinator configured to facilitate acquisition of data from the one or more sensor nodes, where the access coordinator includes a processing module, and where the processing module is configured to transmit a first beacon to the one or more sensor nodes, where the first beacon is configured indicate a start of a new control cycle, transmit a second beacon from the access coordinator to a sensor node transmitting the first data frame, where the second beacon is configured to initiate a polling cycle, and acknowledge receipt of the first data frame.

In accordance with further aspects of the present technique, a system for communicating data in a wireless control area network is presented. The system includes one or more sensor nodes configured to facilitate acquisition of data, where the one or more sensor nodes include a processing module, and where the processing module is configured to prepare data for transmission from the one or more sensor nodes to an access coordinator in response to a first beacon transmitted from an access coordinator to the one or more sensor nodes, where the first beacon is configured to indicate a start of a new communication cycle, generate a first data frame, where the first data frame is indicative of a sensor node having data to transmit, and where the first data frame is configured to create a correlation between a poll packet arrival time and a data arrival time at the one or more sensor nodes, transmit the first data frame from at least one sensor node to an access coordinator, and communicate data from the one or more sensor nodes to an access coordinator in response to the second beacon.

In accordance with further aspects of the present technique, a system for communicating data in a wireless control area network is presented. The system includes an access coordinator configured to facilitate acquisition of data from one or more sensor nodes, where the access coordinator includes a processing module, and where the processing module is configured to transmit a first beacon to one or more sensor nodes, where the first beacon is configured indicate a start of a new control cycle, transmit a second beacon from the access coordinator to a sensor node transmitting a first data frame, where the second beacon is configured to initiate a polling cycle, and acknowledge receipt of the first data frame.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Although the exemplary embodiments of a diagnostic system illustrated hereinafter are described in the context of a patient monitoring system, it will be appreciated that use of the diagnostic system in industrial applications are also contemplated in conjunction with the present technique. More particularly, the diagnostic system may find application in other wireless control-area network like applications, where the control-area network like applications include a central controller configured to control operations of multiple entities. By way of example, the diagnostic system may find application in a manufacturing setting, where a central controller may be configured to control multiple machines. In addition, the diagnostic system may also be used in monitoring and control applications, such as, but not limited to, monitoring and control of turbines, aircraft engines, medical instruments, to name a few, where a central controller may be configured to monitor performance of equipment using sensors and control the sensors using actuators. Furthermore, the diagnostic system may also find application in environment control equipment, where sensors periodically report status at regular intervals to a central controller, and where the central controller may be configured to make decisions based on these inputs from the sensors. Moreover, the diagnostic system may find application in industrial systems such as industrial imaging systems and non-destructive evaluation and inspection systems, such as pipeline inspection systems and liquid reactor inspection systems.

Figure 1:
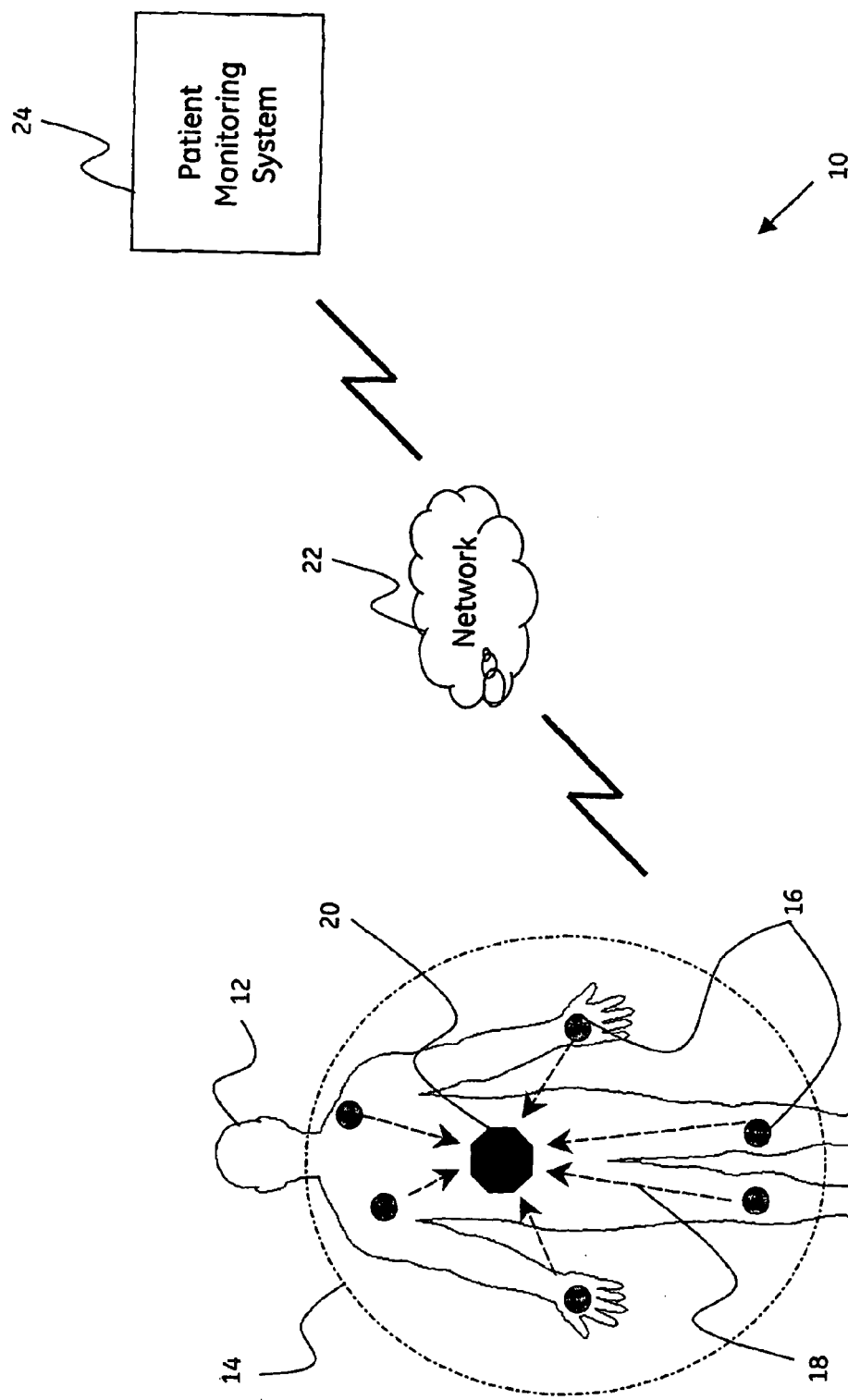
FIG. 1 is a block diagram of an exemplary diagnostic system, in accordance with aspects of the present technique.

FIG. 1 is a block diagram of an exemplary diagnostic system 10, in accordance with aspects of the present technique. The system 10 may be configured to acquire clinical information from a patient 12 via a wireless body area network (WBAN) 14. The data may include physiological data, in certain embodiments. As will be appreciated, the WBAN 14 may include a plurality of body-worn parameter specific sensor nodes 16. These sensor nodes 16 may be operationally coupled to the patient 12. In certain embodiments, the sensor nodes 16 may be physically interfaced with the patient 12 and configured to sense and process physiological data associated with the patient 12. Outputs of the sensor nodes 16 may include waveform data that is representative of a physiological parameter associated with the patient 12. Alternatively, outputs of the sensor nodes 16 may include a discrete value that is indicative of a physiological parameter measurement or a patient parametric value. By way of example, the sensor nodes 16 may include an electrocardiogram (ECG) sensor configured to monitor heart activity, an electromyography (EMG) sensor configured to monitor muscle activity, an electroencephalography (EEG) sensor configured to monitor brain electrical activity, a blood pressure (BP) sensor configured to monitor blood pressure, a tilt sensor configured to monitor trunk position, a breathing sensor configured to monitor respiration, a movement sensor configured to monitor the patient's activity, or combinations thereof. The sensor nodes 16 typically generate signals representative of a corresponding physiological parameter.

Additionally, the WBAN 14 may also include a body-worn access coordinator (AC) 20, where the access coordinator 20 may be configured to poll the sensor nodes 16 for physiological data. The access coordinator 20 may also be configured to aid in collecting and processing the physiological data. Further, the access coordinator 20 may also be configured to include optional data storage and/or a display subsystem, which may be used for presentation and/or alert notification.

The sensor nodes 16 may be configured to communicate any physiological data to the access coordinator 20. In a presently contemplated configuration, the sensor nodes 16 may be configured to wirelessly communicate the physiological data to the access coordinator 20. Reference numeral 18 may be representative of this wireless communication of physiological data from the sensor nodes 16 to the access coordinator 20. It may be noted that although the present embodiment illustrates the physiological data as being wirelessly transmitted from the sensor nodes 16 to the access coordinator 20, other means of data transmission, such as, but not limited to, wired transmission of the physiological data are also contemplated in conjunction with the present technique. The access coordinator 20 may then be configured to transmit the collected physiological data to a data storage system 24, for instance. In certain embodiments, the data storage system 24 may include a patient monitoring system (PMS) disposed within a caregiving facility, such as a hospital. The patient data such as the physiological data acquired by the PMS 24 may then be processed by the PMS 24. The processed data may then be used to aid a clinician in identifying disease states, assessing need for treatment, determining suitable treatment options, and/or monitoring the effect of treatment on the disease states.

In a presently contemplated configuration, the access coordinator 20 may be configured to wirelessly communicate collected physiological data to the PMS 24 via a network 22. It may be noted that although the present embodiment illustrates the physiological data as being wirelessly transmitted from the access coordinator 20 to the PMS 24 via the network 22, other means of data transmission, such as, but not limited to, wired transmission of the physiological data are also contemplated in conjunction with the present technique.

As will be appreciated, in a typical WBAN, the access coordinator controls the operation of the sensor nodes that exist within the WBAN. Using the currently available techniques, the access coordinator polls the sensor nodes in a round-robin fashion according to a predetermined polling sequence. Individual sensor nodes respond whenever polled by the access coordinator. In other words, the access coordinator notifies all the sensor nodes within the WBAN prior to starting a polling cycle, and the individual sensor nodes prepare data, if any, to be transmitted in response to the poll. Subsequently, the access coordinator starts polling the sensor nodes according to the polling sequence. However, data bursts from all the sensor nodes come more or less at the same time instant, disadvantageously leading to the bursts in individual nodes to be substantially synchronized. A challenge in handling this kind of traffic is to optimally poll the sensor nodes and efficiently share the bandwidth for data transfer. Also, duration of the data transfer cycle is not consistent as the data transfer cycle is dependent upon the time taken by the access coordinator to process the acquired data.

It may therefore be desirable to develop a design of a process that may be configured to advantageously overcome the shortcomings of the presently available techniques. More particularly, it may be desirable to minimize the data transfer delay. In addition, it may be desirable for delays associated with the sensor nodes to be as deterministic as possible. Accordingly, a system configured to enhance data transfer in a WBAN, while minimizing data transfer delays, is presented. In accordance with aspects of the present technique, the sensor nodes 16 may include a corresponding processing module (not shown in FIG. 1), where the processing modules may be configured to aid in enhancing the communication of data from the sensor nodes 16 to the access coordinator 20. The processing modules will be described in greater detail with reference to FIGS. 2-9. In accordance with further aspects of the present technique, the access coordinator 20 may also include a processing module (not shown in FIG. 1), where the processing module may be configured to aid in enhancing the data communication from the sensor nodes 16 to the access coordinator 20. This processing module will be described in greater detail with reference to FIGS. 2-9.

Figure 2:
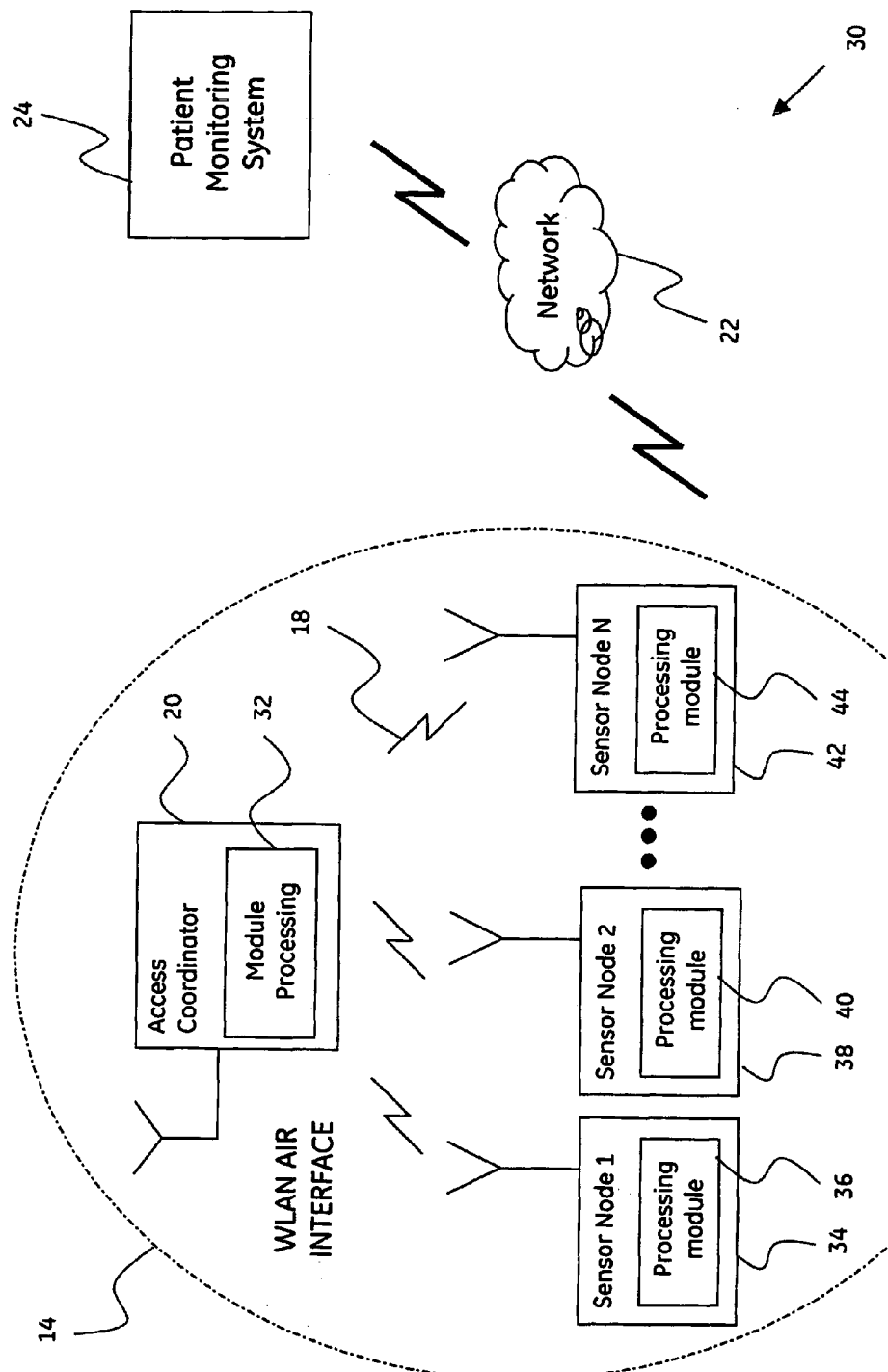
FIG. 2 is a block diagram of an embodiment of the exemplary diagnostic system of FIG. 1, in accordance with aspects of the present technique.

Referring now to FIG. 2, a portion 30 of an embodiment of the diagnostic system 10 of FIG. 1 is illustrated. As previously noted with reference to FIG. 1, the WBAN 14 may include one or more sensor nodes, such as the sensor nodes 16 (see FIG. 1), where the sensor nodes may be configured to aid in obtaining physiological data from the patient 12 (see FIG. 1). In a presently contemplated configuration, the WBAN 14 may include a first sensor node 34, a second sensor node 38, and an $N^{th}$ as sensor node 42. Furthermore, each of the sensor nodes 34, 38, 42 may include a corresponding processing module, where the processing module may be configured to aid in enhancing the transmission of physiological data from the sensor nodes 34, 38, 42 to an access coordinator, such as the access coordinator 20 (see FIG. 1). By way of example, in the example illustrated in FIG. 2, the first sensor node 34 in the WBAN 14 may include a first processing module 36, while the second sensor node 38 may include a second processing module 40. In a similar fashion, the $N^{th}$ sensor node 42 may include an $N^{th}$ processing module 44. As will be appreciated, each of the sensor nodes 34, 38, 42 may include a corresponding protocol stack not shown in FIG. 2), where the protocol stack may include an application layer, a network layer, a media access and control (MAC) layer and a physical layer. In certain embodiments, the processing modules 36, 40, 44 may be configured to reside in a corresponding MAC layer of the respective sensor node 34, 38, 42.

In addition, the access coordinator 20 may also be configured to include a corresponding processing module 32, where the processing module 32 may be configured to enhance the acquisition of data from the sensor nodes 34, 38, 42. The access coordinator 20 may then communicate the data acquired from the sensor nodes 34, 38, 42 to the PMS 24 via the network 22.

Figure 3:
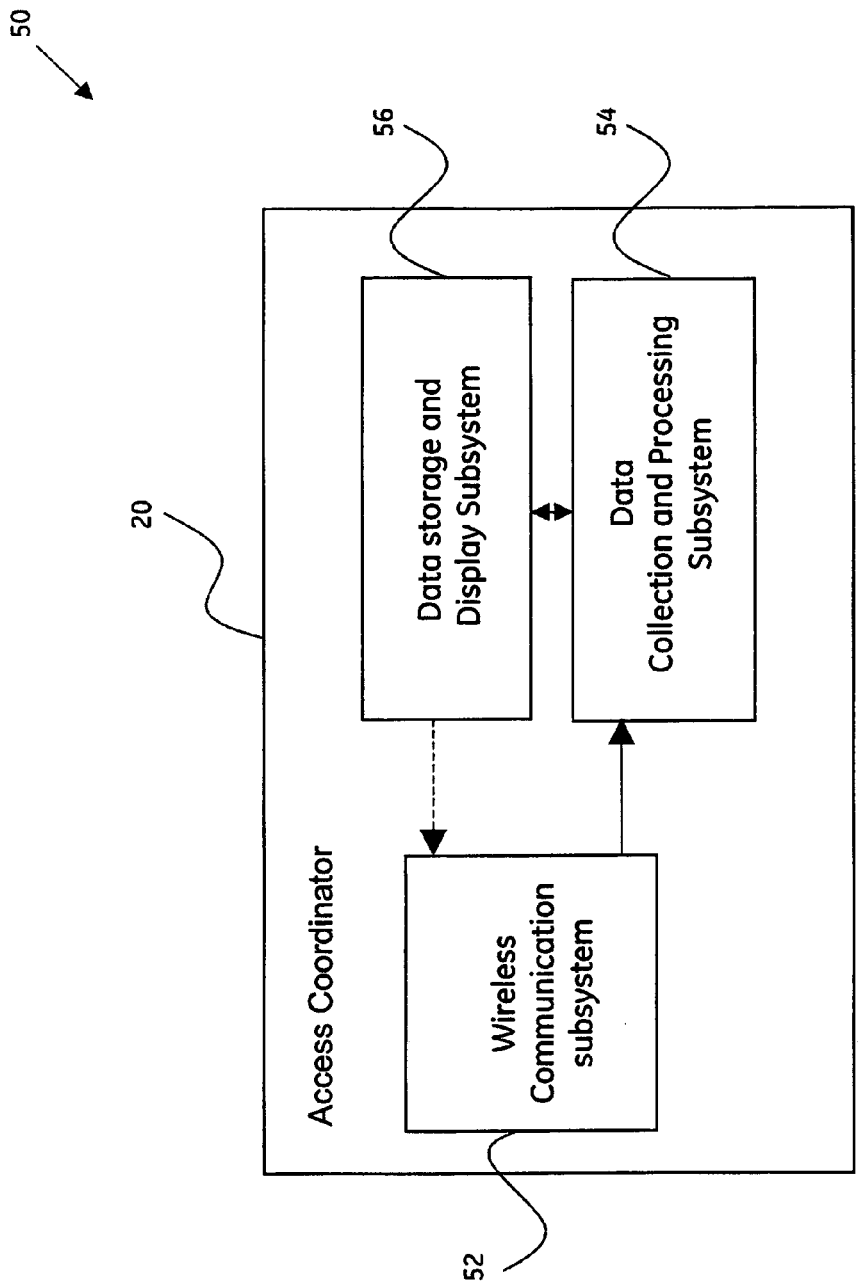
FIG. 3 is a block diagram of an access coordinator for use in the exemplary diagnostic system of FIG. 1, in accordance with aspects of the present technique.

Referring now to FIG. 3, an embodiment 50 of an access coordinator, such as the access coordinator 20 (see FIG. 1) is illustrated. In a presently contemplated configuration, the access coordinator 20 may be configured to include at least three functional subsystems. The access coordinator 20 may include a wireless communication subsystem 52, where the wireless communication subsystem 52 may be configured to poll the sensor nodes in the WBAN for physiological data. In addition, the access coordinator 20 may include a data collection and processing subsystem 54 configured to collect the physiological data and process the collected physiological data. The access coordinator 20 may also include an optional data storage and display subsystem 56 configured to aid in presentation of the physiological data and/or alarm notification. Furthermore, the access coordinator 20 may be configured to communicate the physiological data wirelessly to PMS 24, for example.

Figure 4:
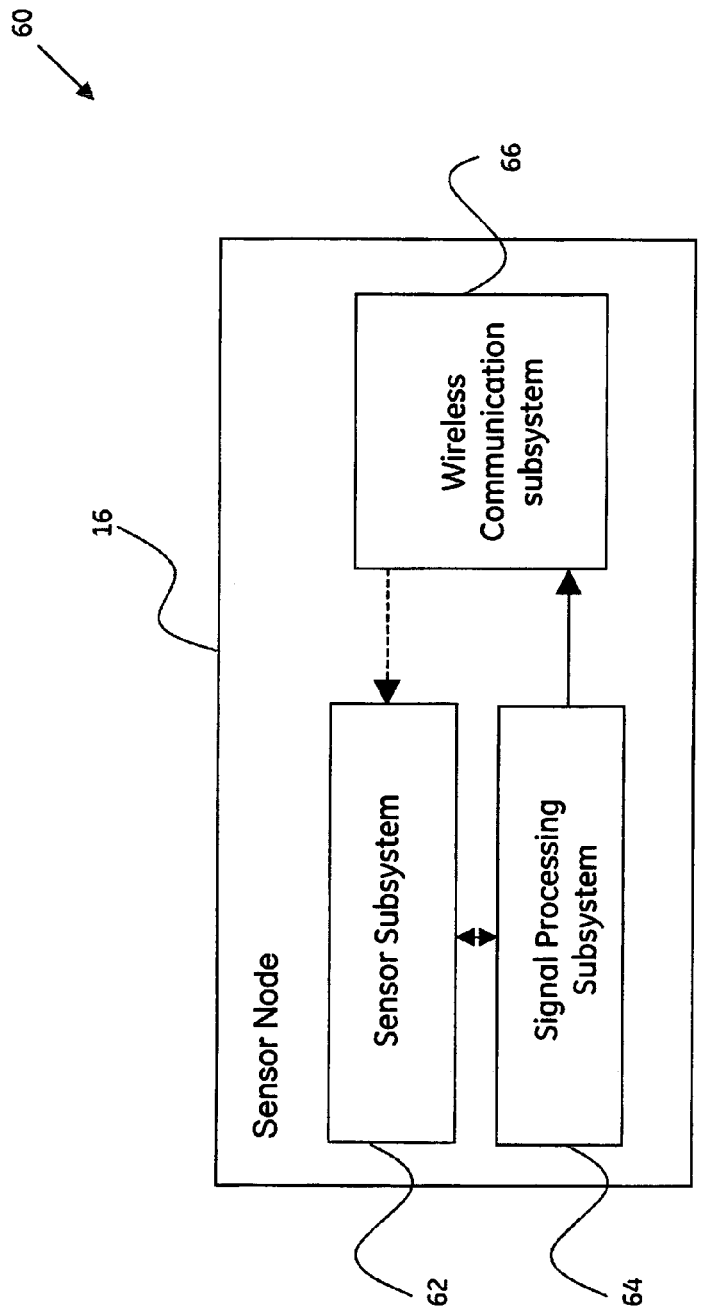
FIG. 4 is a block diagram of a sensor node for use in the exemplary diagnostic system of FIG. 1, in accordance with aspects of the present technique.

FIG. 4 is a diagrammatic illustration of an embodiment 60 of a sensor node, such as the sensor node 16 (see FIG. 1). In a presently contemplated configuration, the sensor node 16 may include at least three main functional subsystems. More particularly, the sensor node 16 may include a sensor subsystem 62, where the sensor subsystem 62 may be configured to physically interface with a patient, such as the patient 12 (see FIG. 1) and to sense the physiological information from the patient 12. Further, the sensor node 16 may also include a signal processing subsystem 64 configured to collect the physiological data from sensor subsystem 62 and perform signal processing and analysis of the collected data. Additionally, the sensor node 16 may also include a wireless communication subsystem 66. The physiological data collected and processed by the signal processing subsystem 64 may then be communicated to an access coordinator, such as the access coordinator 20 (see FIG. 1) using wireless communication subsystem 66. The wireless communication subsystem 66 may also be configured to notify the sensor subsystem 62 to initiate preparation of data for transmission.

As previously described, presently available techniques for communicating physiological data from the sensor nodes to the access coordinator typically involve an unpredictable amount of delay in the communication of data from the sensor nodes to the access coordinator due to the random nature of the data acquisition cycle. For example, some of the sensor nodes may not be able to transmit data during a current polling cycle, as data at the nodes may arrive after the nodes are polled, thereby resulting in a delay in data transmission. Moreover, if a plurality of sensor nodes has data to transmit to the access coordinator, the sensor nodes contend for the transmission channel, thereby resulting in data collisions. Hence, use of the presently available techniques, such as contention-based access techniques, leads to an excessive number of data collisions in the transmission channel, as the data bursts tend to arrive at the individual sensor nodes in a synchronized manner. Also, the presently available techniques, such as contention-free access techniques, start polling the sensor nodes for data immediately after transmitting the beacon and hence fail to provide a correlation between receipt of a beacon and the arrival of data at the sensor nodes, thereby resulting in non-deterministic delays in the transmission of data. Hence, it may be desirable to minimize delays associated with data transfer. Furthermore, it may also be desirable to design a method of communicating data from the sensor nodes to the access coordinator such that the associated delays are substantially deterministic in nature.

Accordingly, a method of communicating data in a WBAN from the sensor nodes to the access coordinator, in accordance with exemplary aspects of the present technique, is presented. More particularly, the method may be configured to optimally poll the sensor nodes for data. Additionally, the sensor nodes may also be configured to efficiently share the channel bandwidth for the transmission of data from the sensor nodes to the access coordinator. In other words, the method of communicating data from the sensor nodes to the access coordinator may be configured to establish a correlation between the arrival of a beacon at the sensor nodes and the arrival of data at the sensor nodes, thereby minimizing delays in data transfer and enhancing efficiency of data transfer.

Figure 5A:
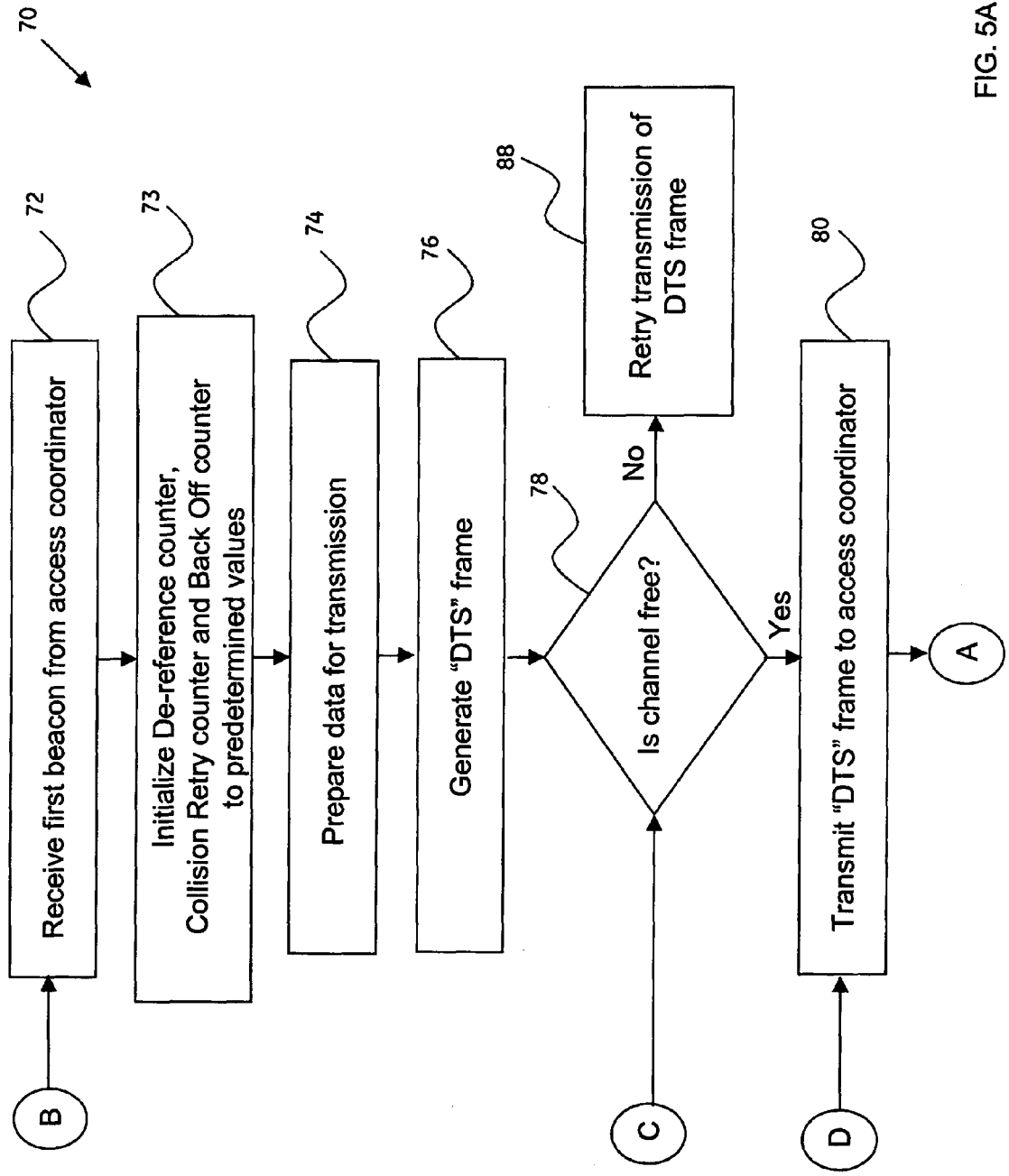
FIGS. 5A-5B are flow charts illustrating an exemplary method of communicating data from sensor nodes to an access coordinator in a wireless body area network, in accordance with aspects of the present technique.
Figure 5B:
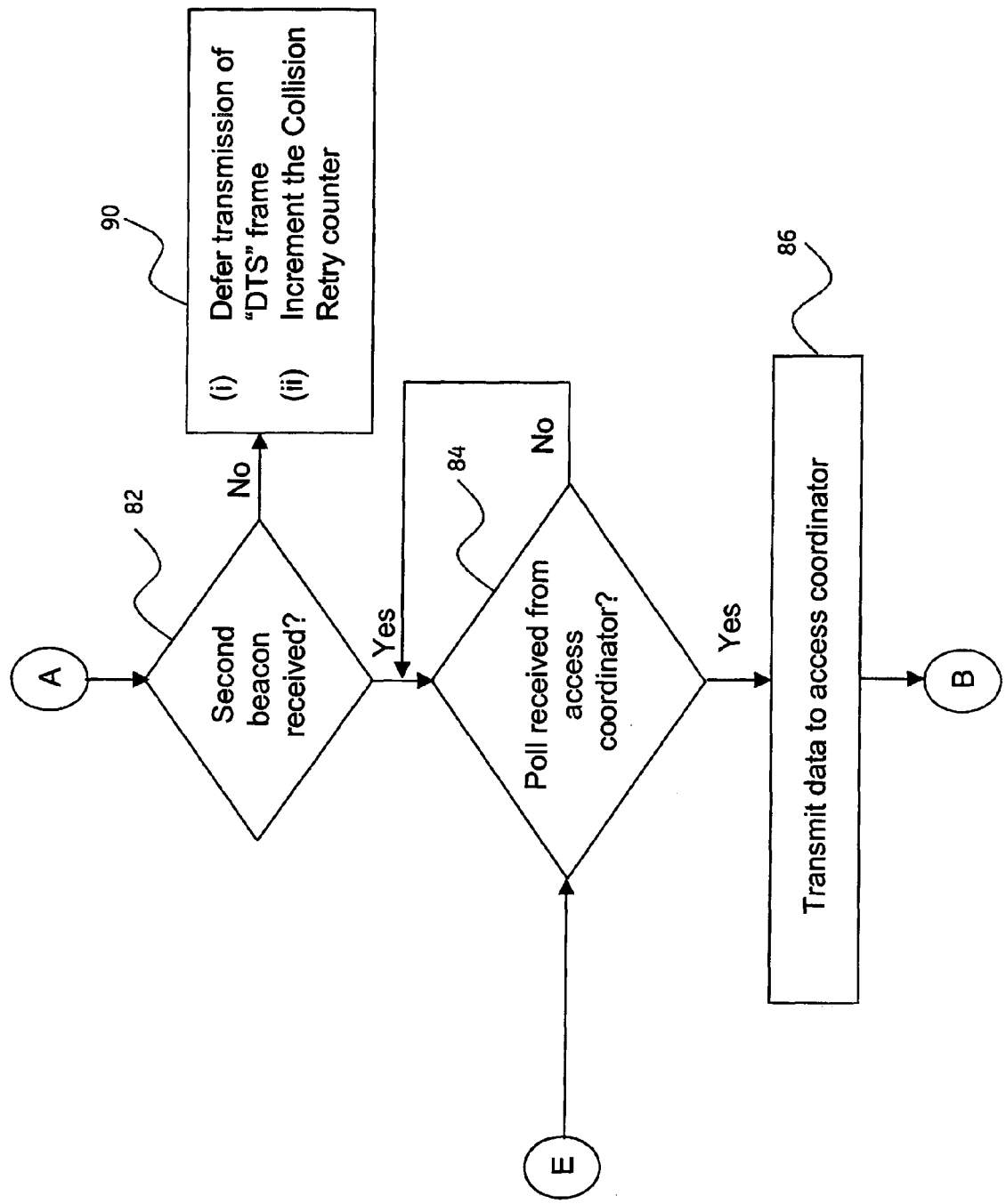

Turning now to FIGS. 5A-5B, a flow chart 70 illustrating an exemplary method of communicating data in a wireless body area network is presented. More particularly, an exemplary method of communicating data from one or more sensor nodes to an access coordinator in the WBAN is presented. The method starts at step 72, where the one or more sensor nodes, such as the sensor nodes 34, 38, 42 (see FIG. 2) in the WBAN, such as the WBAN 14 (see FIG. 1), may receive a first beacon. This first beacon may be transmitted by the access coordinator, such as the access coordinator 20 (see FIG. 2), in the WBAN to the one or more sensor nodes in WBAN. The first beacon transmitted by the access coordinator to the one or more sensor nodes may be configured to notify the sensor nodes of a start of a new data communication cycle. It may be noted that the terms communication cycle and control cycle may be used interchangeably. In accordance with exemplary aspects of the present technique, the access coordinator does not transmit any polling packets at step 72. By not transmitting any poll packets at step 72, the access coordinator allows the sensor nodes time to prepare data for transmission, thereby minimizing delays in data transfer as data may not be available for transmission when the sensor nodes are polled by the access coordinator.

In accordance with further aspects of the present technique, each sensor node may be configured to maintain at least three counters. These counters may include a De-reference counter, a Collision Retry counter and a Back Off counter. These counters may be initialized to predetermined default values, at step 73. The working of these counters and the predetermined default values will be described in greater detail with reference to FIGS. 6-9.

As previously noted, the sensor nodes may be configured to acquire physiological data, such as a blood pressure or a heart rate, from the patient. Once the one or more sensor nodes receive the first beacon, the sensor nodes may be configured to prepare the acquired physiological data for transmission to the access coordinator, as indicated by step 74. In other words, the physiological data may arrive at a MAC layer from an application layer in the protocol stack of the sensor nodes.

As previously noted, use of the presently available techniques disadvantageously results in data transfer delays as the data at the sensor nodes may not be available for transmission when the sensor nodes are polled by the access coordinator. Accordingly, it may be desirable to establish a correlation between the arrival of data at the sensor nodes and poll packets transmitted by the access coordinator to the sensor nodes. More particularly, it may be desirable to create a relationship between a beacon arrival time and the data arrival time at the sensor nodes. In accordance with exemplary aspects of the present technique, a special data frame may be used to create a correlation between the beacon arrival time and the data arrival time at the sensor nodes. This special data frame may be referred to as a "Data to Send" (DTS) frame.

Subsequently, at step 76, a sensor node that is ready to transmit data to the access coordinator may be configured to generate a corresponding DTS frame. In accordance with exemplary aspects of the present technique, the DTS frame may be transmitted from a sensor node to the access coordinator, where the DTS frame may be configured to notify the access coordinator that the sensor node transmitting the DTS frame has data to send. It may be noted that each sensor node having data to transmit may be configured to generate a corresponding DTS frame.

Following the generation of a respective DTS frame, the sensor nodes having the DTS frame may be configured to transmit the DTS frame to the access coordinator. Accordingly, each sensor node may be configured to verify availability of a transmission channel, as indicated by step 78. If the transmission channel is available, then the sensor node having the DTS frame may be configured to communicate the DTS frame to the access coordinator via the transmission channel, at step 80.

Once the access coordinator receives the DTS frame transmitted by a sensor node, the access coordinator may be configured to transmit a second beacon to the sensor node that transmitted the DTS frame and the other sensor nodes. The second beacon may be configured to be indicative of a start of a polling cycle by the access coordinator. In addition, the second beacon may be configured to serve as an acknowledgement of receipt of the DTS frame by the access coordinator. A check may be carried out at step 82 to verify if the sensor node that transmitted the DTS frame received the second beacon. Furthermore, once the access coordinator receives the DTS frame from a sensor node, the access coordinator may be configured to revise a predetermined polling sequence by moving the sensor node that sent the DTS frame to the top of the polling sequence from its original position to generate a revised polling sequence. It may be noted that the positions of the other sensor nodes in the polling sequence may not be changed.

Additionally, at step 82, if it verified that the sensor node received the second beacon, then another check may be carried out at step 84 to check if the sensor node received a poll from the access coordinator. Furthermore, if it is verified that the sensor node received the second beacon, then that sensor node may be configured to transmit data to the access coordinator, as depicted by step 86. It may be noted that the other sensor nodes may also be configured to receive the second beacon transmitted by the access coordinator. Moreover, the other sensor nodes having respective DTS frames may be configured to discard their DTS frames on receipt of the second beacon as the second beacon is indicative of the access coordinator receiving a DTS frame and the start of the polling sequence. The access coordinator may be configured to first poll the sensor node that transmitted the DTS frame, in accordance with the revised polling sequence. Also, the other sensor nodes may be polled as per the revised polling sequence. It may be noted that this revised polling order or polling sequence may be stored in a polling table. Additionally, the polling sequence may be configured to define an order in which the sensor nodes in the WBAN are polled. It may be noted that the terms polling sequence and polling order may be used interchangeably.

Once the access coordinator completes polling the sensor nodes as per the revised polling sequence, the access coordinator may be configured to issue a data frame, where the data frame may be configured to be indicative of a completion of the current polling sequence. This data frame may be referred to as a "Communication Cycle End" (CC-End) frame. Steps 72-86 may then be repeated.

Figure 6:
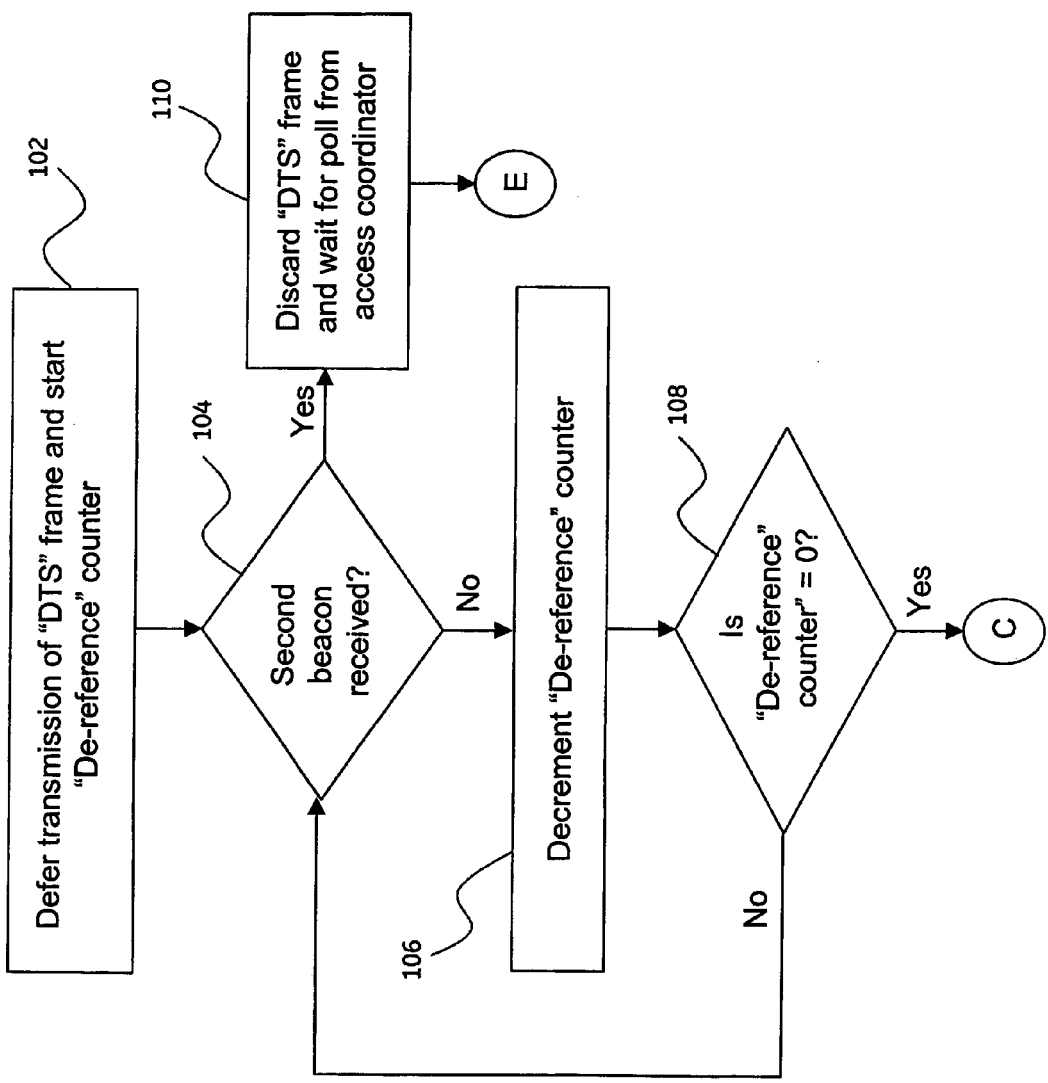
FIG. 6 is a flow chart illustrating an exemplary method of retrying transmission of a data frame, in accordance with aspects of the present technique.

With returning reference to the decision block 78, if it is verified that the transmission channel is not free, then the sensor node attempting to transmit the DTS frame to the access coordinator may be configured to retry to transmit the DTS frame, as indicated by step 88. Step 88 may be better understood with reference to FIG. 6. Referring now to FIG. 6, a flow chart illustrating step 88 (see FIG. 5) is illustrated. More particularly, an exemplary method of attempting to retry transmission of the DTS frame from the sensor node to the access coordinator of step 88 is depicted.

The method starts at step 102, where the sensor node attempting to transmit the corresponding DTS frame to the access coordinator may be configured to defer the transmission of the DTS frame. In addition, the sensor node may be configured initialize a De-reference counter. This De-reference counter may be configured to aid the sensor node in attempting to retry transmission the DTS frame. In other words, the De-reference counter may be configured to aid the sensor node in waiting for a predetermined time period before checking the transmission channel for availability. In certain embodiments, the De-reference counter may be initialized to a value of about ($2^p*CW_{min}$) slots, where p may be an integer having a value in a range from about 6 to about 8 and $CW_{min}$ may be indicative of a minimum Contention Window value, where the minimum Contention Window may be selected based on a physical layer modulation scheme. By way of example, for a Orthogonal Frequency Division Multiplexing (OFDM) scheme the $CW_{min}$ value may include about 15 slots with a slot time of about 9 microseconds and for a Complementary Code Keying (CCK) scheme, the $CW_{min}$ may include about 31 slots with a slot time of 20 microseconds. In certain embodiments, the De-reference counter value may be chosen depending on the application and the number of sensor nodes in the WBAN. By deferring the transmission of the DTS frames from a plurality of sensor nodes, data collisions in the transmission channel may be substantially reduced, and hence unpredictable delays in the transfer of data from the sensor nodes to the access coordinator may be substantially reduced.

Subsequently, at step 104, a check may be carried out to verify if a beacon, such as the second beacon, is received by the sensor node under consideration. As previously noted, the access coordinator may be configured to transmit the second beacon to the sensor nodes in response to receipt of a DTS frame from a sensor node in the WBAN. At step 104, if it is verified that the sensor node attempting to transmit the corresponding DTS frame received the second beacon transmitted by the access coordinator, then that sensor node may be configured to discard the corresponding DTS frame and wait for a poll from the access coordinator, as indicated by step 110. In other words, if the sensor node receives the second beacon, then it may be understood that another sensor node has successfully transmitted a DTS frame to the access coordinator and consequently, the access coordinator has issued the second beacon.

However, at step 104, if it is verified that the sensor node did not receive the second beacon, then the sensor node may be configured to decrement the De-reference counter, as depicted by step 106. Further, a check may be carried out at step 108 to verify if the De-reference counter has a value of zero. If the De-reference counter has been decremented to have a value of about zero, then control may be returned to step 78 (see FIG. 5). However, at step 108, if it is verified that the De-reference counter has a non-zero value, then control may be returned to step 104. The sensor node may then repeat steps 104-108 until the De-reference counter has a value of about zero. By implementing the De-reference counter as described hereinabove, the sensor node may be configured to wait for a predetermined time interval before attempting to transmit the DTS frame, thereby circumventing data collisions.

The method described with reference to FIG. 6 may be referred to as a "Sense and Deny" protocol. In other words, the sensor node having a DTS frame may be configured to "sense" the availability of the transmission channel. More particularly, the sensor node may be configured to transmit the DTS frame to the access coordinator only if the transmission channel is available. However, if the transmission channel if busy, the sensor node may be configured to "defer" or "deny" the transmission of the DTS frame to the access coordinator. More particularly, the De-reference counter may be configured to compel the sensor node to "wait" for a predetermined time period before trying to recheck the availability of the transmission channel. In addition, since a check is carried out to verify if the sensor node has received the second beacon from the access coordinator, where the second beacon is representative of acknowledgement from the access coordinator of receipt of a DTS frame from a sensor node in the WBAN, collisions between sensor nodes trying to transmit respective DTS frames may be circumvented. Moreover, the sensor nodes having DTS frames may be configured to discard their DTS frames and wait for a poll by the access coordinator, thereby reducing any delays in the transfer of data from the sensor nodes to the access coordinator.

With returning reference to FIG. 5, and more particularly to step 82, if it is verified that the second beacon was not received by the sensor nodes, then those sensor nodes may be configured to defer the transmission of corresponding DTS frames, as indicated by step 90. As will be appreciated, the sensor nodes that do not receive the second beacon may attempt to transmit corresponding DTS frames, thereby resulting in collisions between data from the various sensor nodes. Additionally, the sensor nodes may be configured to increment the Collision Retry counter by 1, as indicated by step 90. The Collision Retry counter will be described in greater detail with reference to FIG. 7. In accordance with aspects of the present technique, the sensor nodes that experience collision may be configured to retry transmission of corresponding DTS frames after a predetermined time period. This time period may be referred to as a "Back Off" period. This method of avoiding collisions between sensor nodes attempting to transmit DTS frames may be better understood with reference to FIG. 7.

Figure 7A:
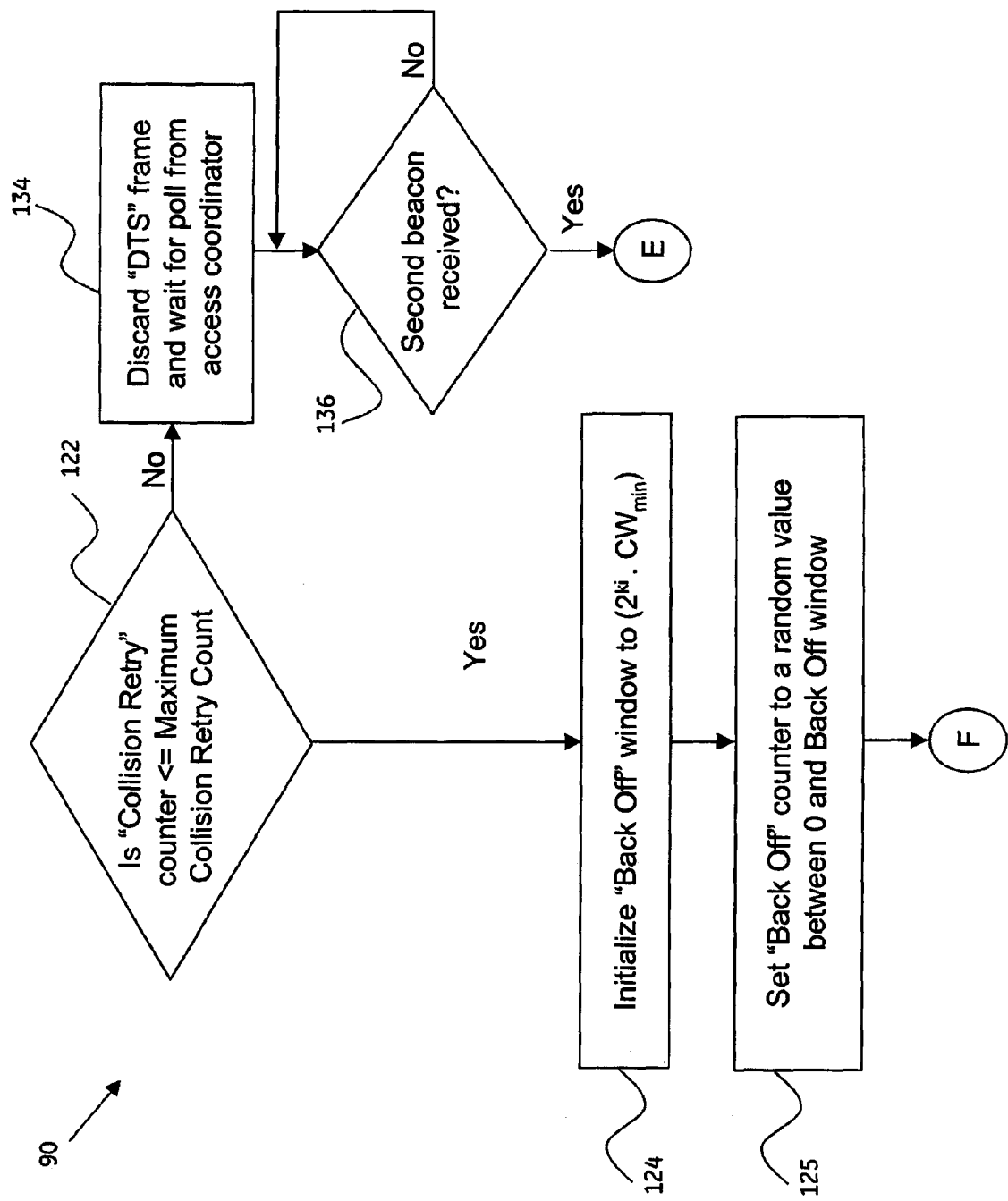
FIGS. 7A-7B are flow charts illustrating an exemplary method of deferring communication of a data frame from the sensor nodes to the access coordinator in a wireless body area network, in accordance with aspects of the present technique.
Figure 7B:
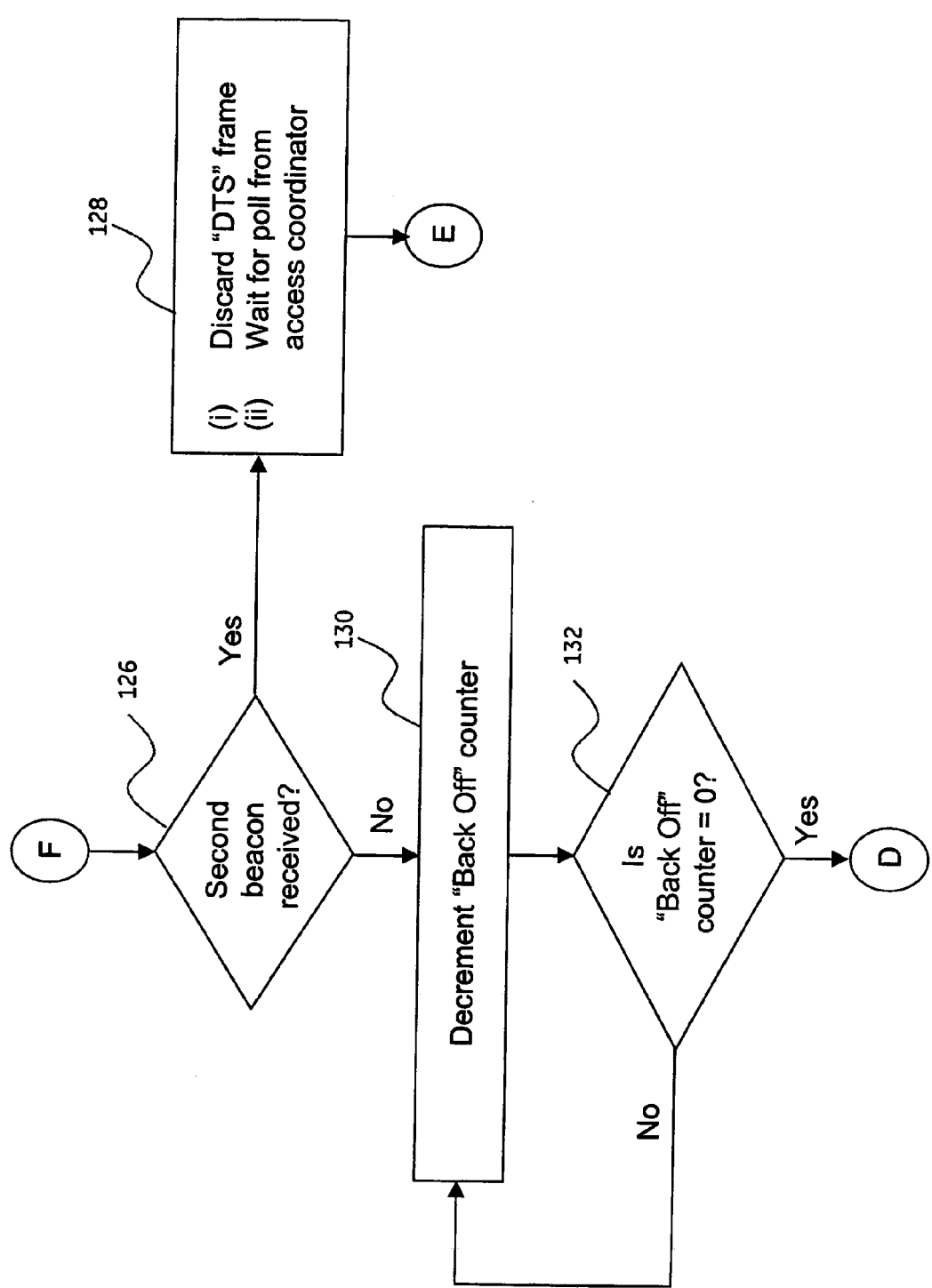

Turning now to FIGS. 7A-7B, a flow chart illustrating step 90 (see FIG. 5) is depicted. More particularly, an exemplary method of circumventing collisions between two or more sensor nodes of step 90 is depicted. In accordance with aspects of the present technique, the sensor nodes may be allowed a predetermined number of attempts to retry transmission of the respective DTS frames. Accordingly, a counter may be set up, where the counter may be indicative of a number of retries attempted by the sensor node to send the DTS frame. This counter may be referred to as a Collision Retry counter. Also, there exists a maximum number of permissible attempts for the sensor nodes to retry transmission of the respective DTS frames, before discarding the DTS frame transmission. This count may generally be referred to as a "Maximum Collision Retry Count". The Maximum Collision Retry Count value may be chosen depending on the application and/or the number of sensor nodes in the WBAN.

The method starts at steps 122, where a check may be carried out to verify if a value of the Collision Retry counter is less than a predetermined maximum value (Maximum Collision Retry Count). If it is verified that the maximum number of retries has not been exceeded, then another counter, a "Back Off" counter may be initialized. Accordingly, at step 124, a "Back Off Window" may be initialized. The Back Off Window may have a value that may be chosen depending on the application and the number of sensor nodes in the WBAN. In one embodiment, the Back Off Window may be configured to have a value of $(2^{ki}*CW_{min})$, where k may be an integer having a value in a range from about 3 to about 4, and i may be representative of a value of the Collision Retry counter. In accordance with exemplary aspects of the present technique, the Back Off counter may be initialized to a randomly selected value in a range from about 0 to about $[2^{ki}*CW_{min}]$ (Back Off Window), as indicated by step 125. The Back Off counter may be configured to aid the sensor nodes "backing off" from attempting to retry transmitting the DTS frames to the access coordinator.

Subsequently, at step 126, a check may be carried out to re-verify if the second beacon is received by the sensor node. As previously noted, the second beacon may be indicative of an acknowledgment of receipt of a DTS frame transmitted by a sensor node in the WBAN. Accordingly, at step 126, if it is verified that the sensor node received the second beacon, then that sensor node may be configured to discard the corresponding DTS frame, as indicated by step 128. In addition, at step 128, the sensor node may also be configured reset the collision retry and back off counters to zero. Moreover, at step 128, the sensor node may also be configured to wait for a poll from the access coordinator to facilitate transmission of data to the access coordinator. Control may then be returned to step 84 (see FIG. 5).

However, at step 126, if it is verified that the sensor node did not receive the second beacon, then the sensor node may be configured to decrement the Back Off counter, as depicted by step 130. Subsequently, a check may be carried out at step 132 to verify if the Back Off counter has a value of zero. If the Back Off counter has a value of zero, then control may be returned to step 80 (see FIG. 5). On the other hand, if it is verified that the Back Off counter has a non-zero value, then the Back Off counter may be decremented until the Back Off counter has a value of zero. In other words, steps 130-132 may be repeated until the back off counter has a value of about zero, and control may be returned to step 80, once the Back Off counter has a value of zero. The method described in steps 122-132 may be referred to as a "Rapid Back Off" method.

Figure 8A:
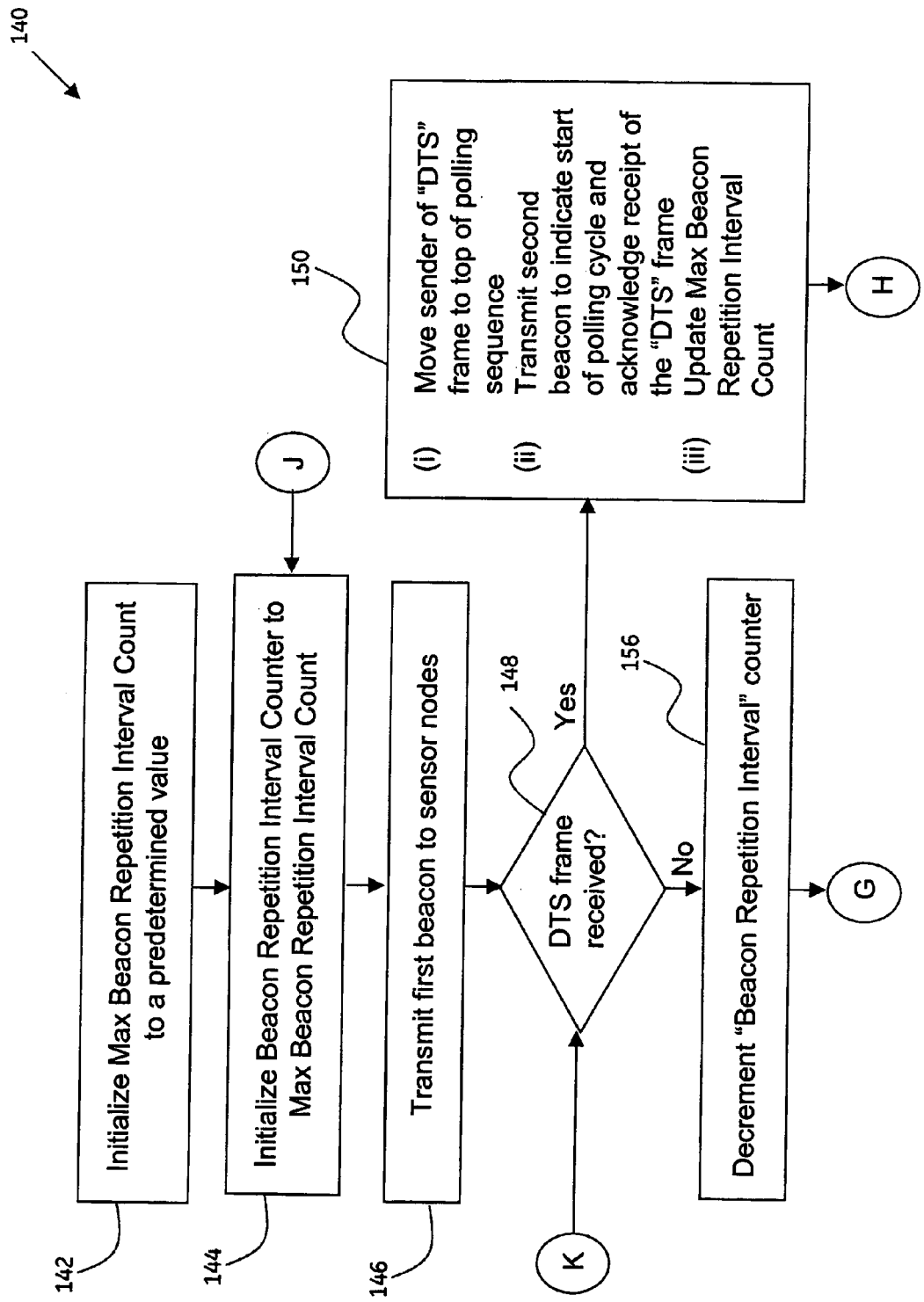
FIGS. 8A-8B are flow charts illustrating an exemplary method of controlling communication of data from the sensor nodes to the access coordinator in a wireless body area network, in accordance with aspects of the present technique.
Figure 8B:
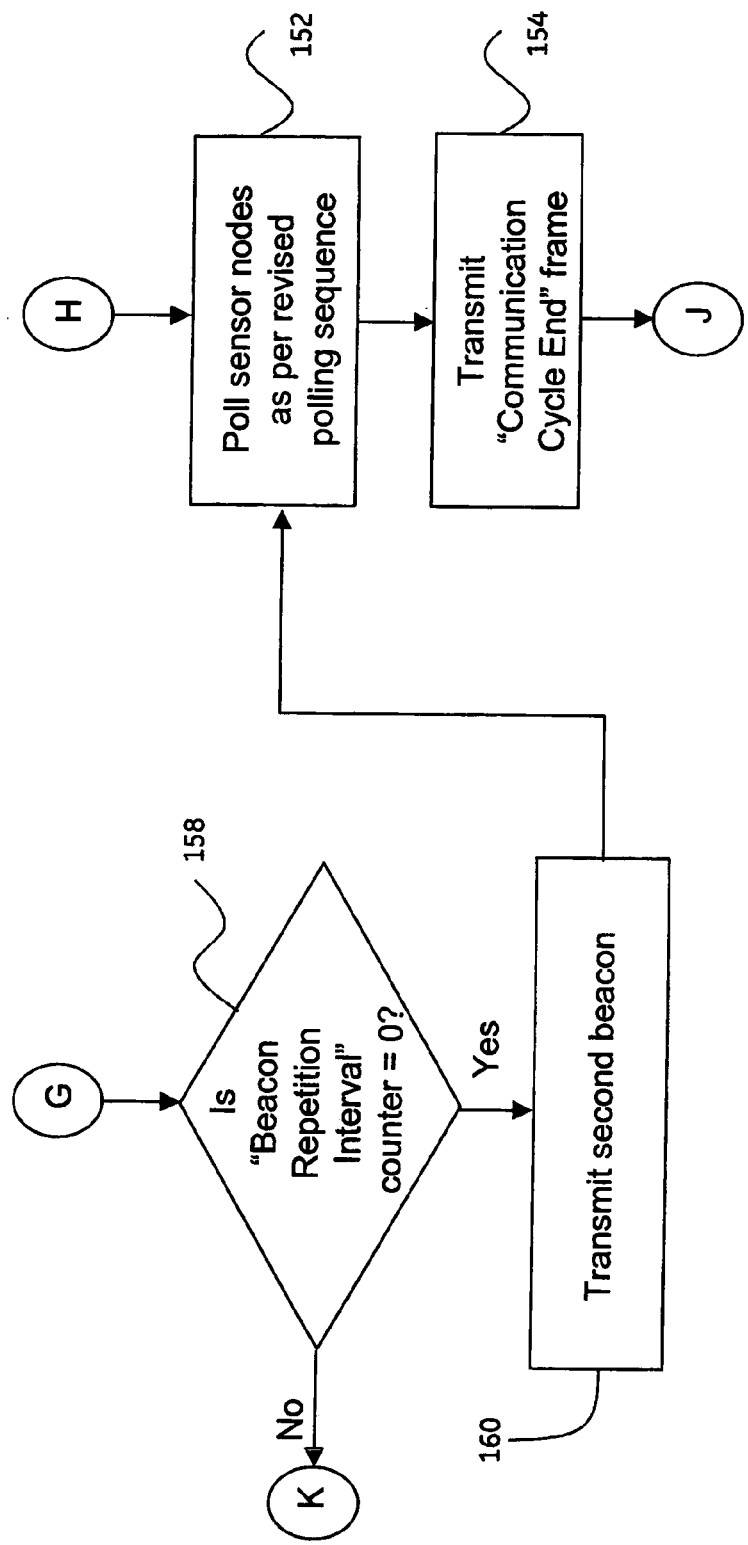

Methods of communicating data from the sensor nodes in the WBAN to the access coordinator are described with reference to FIGS. 5-7. The working of the access coordinator may be better understood with reference to FIG. 8. Referring now to FIGS. 8A-8B, a flow chart 140 illustrating working of an access coordinator, such as the access coordinator 20 (see FIG. 1) in a WBAN, such as the WBAN 14 (see FIG. 1), is depicted. More particularly, the role of the access coordinator in the exemplary method of communicating data from the sensor nodes to the access coordinator is illustrated.

The method starts at step 142, where a Maximum Beacon Repetition Interval may be initialized to a predetermined value. In accordance with aspects of the present technique, the access coordinator may also be configured to wait for a subsequent beacon to start another polling cycle. This interval between two subsequent beacons may be referred to as a "Maximum Beacon Repetition Interval". Further, a count indicative of the Maximum Beacon Repetition Interval may be set up. In one embodiment, the Maximum Beacon Repetition Interval count may be initialized to have a maximum value of a communication cycle period at step 142. It may be noted that the control/communication cycle period may be representative of the time elapsed from the start of a first beacon to the Control Cycle-End (CC-End) frame. In each communication cycle, after the successful reception of DTS frame, the access coordinator may be configured to transmit the second beacon. Furthermore, a Maximum Beacon Repetition Interval Count, may be updated with the time elapsed between the first beacon and the second beacon at step 146. Updating the Maximum Beacon Repetition Interval Count as described hereinabove facilitates adaptive learning for the Maximum Beacon Repetition Interval Count.

In certain embodiments, the predetermined value may be dependent on a communication cycle time interval. By way of example, in one embodiment, the Maximum Beacon Repetition Interval may be initialized to a value of (0.75*Communication Cycle time). The access coordinator may be configured to maintain a counter referred to as a "Beacon Repetition Interval" counter. In one embodiment, the Beacon Repetition Interval counter may be initialized to have a value of the "Max Beacon Repetition Interval Count", as depicted by step 144. The Beacon Repetition Interval counter may be configured to aid the access coordinator in waiting for a predetermined time interval before starting the next polling cycle.

Subsequently, at step 146, where the access coordinator may be configured to transmit a first beacon to the one or more sensor nodes in the WBAN. The first beacon may be configured to notify the sensor nodes of a start of a new communication cycle. It may be noted that in accordance with exemplary aspects of the present technique, the access coordinator may be configured to defer transmission of any poll packets to the sensor nodes, where the poll packets may be configured to poll the sensor nodes for data. By not issuing any poll packets following the first beacon, the sensor nodes may be allowed to prepare data for transmission, and hence loss of data transmitted from the sensor nodes to the access coordinator may be substantially minimized.

As described with reference to FIG. 5, the sensor nodes may be configured to generate respective DTS frames and transmit the DTS frames to the access coordinator, where the DTS frames may be configured to notify the access coordinator that the sensor nodes are ready to transmit data. Accordingly, a check may be carried out at step 148 to verify if the access coordinator received a DTS frame from any sensor node. At step 148, if it is verified that the access coordinator received the DTS frame, then the access coordinator may be configured to move the sender (sensor node) of the DTS frame to the top of the polling sequence from its original position in the polling sequence, as indicated by step 150. In other words, the access coordinator may be configured to generate a revised polling sequence. It may be noted that the order of the other sensor nodes in the polling sequence will remain unchanged. Additionally, at step 150, the access coordinator may also be configured to generate and transmit a second beacon to the sensor nodes in the WBAN. As previously noted with reference to FIG. 5, the second beacon may be configured to notify the sensor nodes of a start of the polling cycle by the access coordinator. The second beacon may also be configured to serve as an acknowledgement of receipt of the DTS frame from the sending sensor node. Also, at step 150, the access coordinator may be configured to update the Max Beacon Repetition Interval Count value with the time elapsed between the first beacon and the second beacon.

Subsequently, at step 152, the access coordinator may be configured to poll the sensor nodes as per the revised polling sequence. Furthermore, once the access coordinator completes the current polling sequence, the access coordinator may be configured to generate a special frame that may be configured to be indicative of an end of the current polling sequence, as depicted by step 154. This frame may generally be referred to as a "Control Cycle End" (CC-end) frame. The access coordinator may be configured to transmit the CC-End frame to the sensor nodes. Moreover, the access coordinator may be configured to start a new communication cycle by initializing the Beacon Repetition Interval counter to the Maximum Beacon Repetition Interval Count and subsequently sending a first beacon as indicated by steps 144-146. In other words, control may be returned to step 144.

With returning reference to the decision block 148, if it is verified that the DTS frame was not received by the sensor node, then the access coordinator may be configured to decrement the Beacon Repetition Interval counter, as depicted by step 156. A check may be carried out at step 158 to verify if the Beacon Repetition Interval counter has a value of zero. Accordingly, at step 158, if it is verified that the Beacon Repetition Interval counter has a value of zero, then the second beacon may be transmitted by the access coordinator, at step 160. Subsequently, control may be returned to step 152, thereby allowing starting of a new polling cycle. Referring again to the decision block 158, if it is verified that the Beacon Repetition Interval counter has a non-zero value, then control may be returned to step 148. By implementing the working of the access coordinator as described hereinabove, the access coordinator may be configured to wait for the DTS frame or Beacon Repetition Interval counter to elapse before starting a subsequent polling cycle, thereby enhancing the communication of data from the sensor nodes to the access coordinator.

Figure 9:
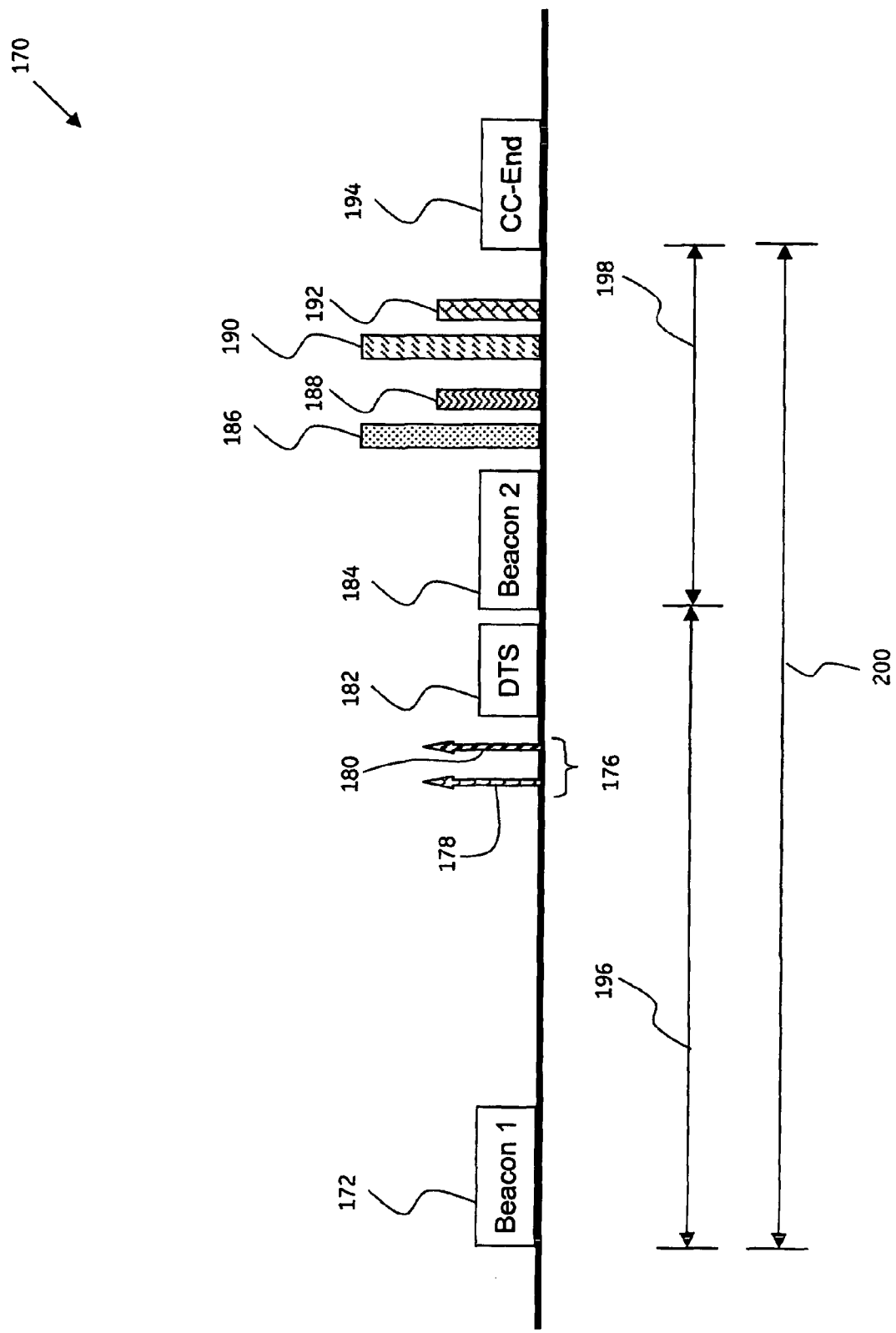
FIG. 9 is a diagrammatic illustration of the exemplary method of communicating data of FIGS. 5-8, in accordance with aspects of the present technique.

The exemplary method of communicating data from the sensor nodes to the access coordinator in a WBAN described with reference to FIGS. 5-8 may be better understood with reference to FIG. 9. A diagrammatic illustration 170 of an exemplary method of communicating data in a WBAN is depicted in FIG. 9. It may be noted that FIG. 9 illustrates a method of communicating data in a two node environment. More particularly, FIG. 9 illustrates a method of communicating data from a first sensor node, such as the first sensor node 34 (see FIG. 2), and a second sensor node, such as the second sensor node 38 (see FIG. 2), to an access coordinator, such as the access coordinator 20 (see FIG. 1), where a WBAN, such as the WBAN 14 (see FIG. 1), may be configured to include the first and second sensor nodes 34, 38 and the access coordinator 20.

The access coordinator 20 may be configured to transmit a first beacon 172 to the first and second sensor nodes 34, 38 in the WBAN 14. As previously noted, the first beacon 172 may be configured to notify the first and second nodes 34, 38 of a start of a communication cycle in the WBAN 14. On receiving the first beacon 172, the sensor nodes 34, 38 may be configured to prepare data for transmission to the access coordinator 20. Further, the access coordinator 20 may be configured to not issue any poll packets with the first beacon 172, thereby allowing the sensor nodes 34, 38 sufficient time to prepare data for transmission to the access coordinator 20. It may be noted that in certain situations, more particularly, using the presently available contention-free access techniques, data may not have arrived at the MAC layer in the sensor nodes 34, 38 by the time a poll packet is received by the sensor nodes 34, 38. In other words, the sensor nodes 34, 38 may not be "ready" to transmit data to the access coordinator when polled, thereby leading to unpredictable delays in the transfer of data.

Subsequent to receipt of the first beacon 172, the sensor nodes 34, 38 may be configured to prepare data for transmission to the access coordinator 20. Reference numeral 176 may generally be representative of data bursts at the sensor nodes 34, 38. More particularly, reference numeral 178 may be indicative of a data burst at the first sensor node 34, while a data burst at the second sensor node 38 may generally be represented by reference numeral 180. Once the data bursts 178, 180 respectively arrive at the first and second sensor nodes 34, 38, the first and second sensor nodes 34, 38 may be configured to generate corresponding DTS data frames. As previously noted, these DTS frames may be transmitted from the sensor nodes 34, 38 to the access coordinator 20, where the DTS frames may be configured to notify the access coordinator 20 about the readiness of the sensor nodes 34, 38 to transmit data 178, 180 to the access coordinator 20.

In accordance with aspects of the present technique, the two sensor nodes 34, 38 may check the availability of a transmission channel to transmit respective DTS frames to the access coordinator 20. In the present example, it may be assumed that the first sensor node 34 transmits the corresponding DTS frame to the access coordinator 20 via the transmission channel. Reference numeral 182 may generally be representative of the DTS frame corresponding to the first sensor node 34. The second sensor node 38 may also attempt to transmit the corresponding DTS frame, namely a second DTS frame (not shown in FIG. 9). However, on finding the transmission channel busy communicating the first DTS frame 182 to the access coordinator 20, the second sensor node 38 may be configured to attempt to retry transmission of the second DTS frame after a predetermined amount of time, thereby circumventing any collision with the transmission of the first DTS frame 182 in the transmission channel. More particularly, the second sensor node 38 may be configured to run the "Sense and Deny" protocol described with reference to FIG. 6. In other words, the second sensor node 38 may be configured to defer transmission of the second DTS frame. The second sensor node 38 may then be configured to carry out a check to verify if a second beacon is received, where the second beacon may be indicative of receipt of a DTS frame by the access coordinator 20. If it is verified that the second sensor node 38 received the second beacon, then the second sensor node 38 may be configured to discard the second DTS frame, and wait for a poll from the access coordinator 20. However, if it is verified that the second sensor node 38 did not receive the second beacon, then the second sensor node 38 may be configured to wait for a predetermined time period to elapse before attempting to transmit the second DTS frame.

Once the access coordinator 20 receives the first DTS frame 182 from the first sensor node 34, the access coordinator 20 may be configured to move the sender of the first DTS frame 182, namely the first sensor node 34, to the top of the polling sequence from the original position of the first sensor node 34 in the polling sequence, thereby generating a revised polling sequence. Moreover, the access coordinator 20 may be configured to issue a second beacon 184 to the first and second sensor nodes 34, 38. The second beacon 184 may be configured to acknowledge receipt of the first DTS frame 182. In addition, the second beacon 184 may also be configured to notify the first and second sensor nodes 34, 38 of a start of polling of data by the access coordinator 20. The access coordinator 20 may then be configured to poll the first and second sensor nodes 34, 38 for data as per the revised polling sequence.

Furthermore, if it is verified that the first sensor node 34, for example, did not receive the second beacon 184, then the first sensor node 34 may be configured to assume that second beacon 184 has collided with a DTS frame associated with another sensor node, and may be configured to run the "Rapid Back Off" protocol as previously described with reference to FIG. 7. More particularly, the first sensor node 34 may be configured to verify if the first sensor node 34 has exceeded a predetermined number of retries attempting to transmit of the DTS frame. If the maximum number of retries has not been exceeded, then the first sensor node 34 may be configured to initialize a Back Off Window using ($2^{ki}*CW_{min}$) where k is an integer and i is representative of the Collision Retry counter value. The Back Off counter may be selected as a random value between 0 and ($2^{ki}*CW_{min}$). Also, the Back Off counter may be configured to aid the first sensor node 34 in waiting for a predetermined time interval to elapse before attempting to transmit the second DTS frame. However, if the first sensor node 34 receives the second beacon 184 during this Back Off counter waiting period, then the first sensor node 34 may be configured to discard the DTS frame and wait for a poll from the access coordinator 20.

The first and second sensor nodes 34, 38 may be configured to verify receipt of the second beacon 184. By way of example, if the first sensor node 34 received the second beacon 184, then the first sensor node 34 may be configured to carry out a check to verify if a poll packet was received from the access coordinator 20. If it is verified that the first sensor node 34 received a poll packet from the access coordinator 20, then the first sensor node 34 may be configured to transmit the data 178 to the access coordinator 20. However, if it is verified that the first sensor node 34 did not receive the poll packet from the access coordinator 20, then the first sensor node 34 may be configured to wait for the receipt of the poll packet from the access coordinator 20. Furthermore, the second sensor node 38 may also be configured to wait for poll packet from access coordinator 20 to transmit the data.

With continuing reference to FIG. 9, reference numeral 186 may be representative of a poll packet received by the first sensor node 34, while a first data packet transmitted by the first sensor node 34 to the access coordinator 20 in response to the first poll packet 186 may generally be represented by reference numeral 188. In a similar fashion, the second sensor node 38 may receive a poll packet 190 from the access coordinator 20. The second sensor node 38 may be configured to transmit a second data packet 192 to the access coordinator 20 in response to the poll packet 190. Furthermore, once the polling sequence is completed, the access coordinator 20 may be configured to issue a CC-End frame 194, where the CC-End frame 194 may be configured to be indicative of a completion of the current communication cycle.

Furthermore, if the access coordinator 20 does not receive a DTS frame from a sensor node, the access coordinator 20 may be configured to wait for a predetermined time period and transmit a second beacon once the predetermined time period has elapsed. This predetermined time period may generally be referred to as a Beacon Repetition Interval 196. Also, reference numeral 198 may be representative of a data transfer period, while the communication cycle period may be represented by reference numeral 200.

The exemplary system for enhanced communication and the method for communication described hereinabove dramatically enhance clinical workflow and patient care as the system may be configured to provide predictable latencies for physiological data transfer between body-worn sensor nodes and a body-worn access coordinator. In addition, the method presented hereinabove may be configured to transmit the bursty and repetitive data traffic with a substantially minimal delay that is deterministic in nature. Also, a means for synchronization between the start of the polling sequence and the availability of data at the sensor nodes may be provided. In other words, the sensor nodes may be configured to notify the access coordinator about the arrival of data in the sensor node and create a relationship between events in the access coordinator and events in the sensor nodes. More particularly, a correlation between the poll packets from the access coordinator and data arrival at the sensor nodes may be created via the DTS frame. Additionally, collisions between sensor nodes attempting to transmit corresponding DTS frames to the access coordinator may be resolved in a speedy manner via use of the "Sense and Deny" and "Rapid Back Off" techniques.

The above-description of the embodiments of the WBAN and the method for communication of data in the WBAN have the technical effect of enhancing clinical workflow as delays in the transmission of data from the sensor nodes to the access coordinator may be substantially minimized. Additionally, collision of sensor nodes attempting to transmit respective DTS frames may be dramatically reduced via introduction of delays of predetermined time intervals.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for communicating data in a wireless control area network, wherein the wireless control area network comprises:
   one or more sensor nodes configured to facilitate acquisition of patient data;
   an access coordinator configured to facilitate acquisition of the patient data from the one or more sensor nodes;
   the method comprising creating a correlation between one or more poll packets from an access coordinator and time of arrival of data at one or more sensor nodes, wherein creating a correlation comprises:

transmitting a first beacon from the access coordinator to the one or more sensor nodes, wherein the first beacon is configured to indicate a start of a new communication cycle;

preparing data for transmission from the one or more sensor nodes to the access coordinator in response to the first beacon;

generating a first data frame, wherein the first data frame is indicative of a sensor node having data to transmit, and wherein the first data frame is configured to create the correlation between a poll packet arrival time and a data arrival time at the one or more sensor nodes;

transmitting the first data frame from at least one sensor node to the access coordinator;

transmitting a second beacon from the access coordinator to the sensor node transmitting the first data frame, wherein the second beacon is configured to initiate polling of data from the one or more sensor nodes; and communicating data from the one or more sensor nodes to the access coordinator in response to the second beacon, wherein the second beacon is further configured to acknowledge receipt of the first data frame.

2. The method of claim 1, further comprising generating a revised polling sequence by moving a sender of the first data frame to the top of a predetermined polling sequence.

3. The method of claim 1, wherein transmitting the first data frame from a sensor node to the access coordinator further comprises:

verifying availability of a transmission channel prior to transmitting the first data frame; and transmitting the first data frame from the sensor node to the access coordinator over the available transmission channel.

4. The method of claim 3, further comprising deferring transmission of the first data frame based on the availability of the transmission channel.

5. The method of claim 4, further comprising verifying receipt of a second beacon.

6. The method of claim 5, further comprising:
discarding the first data frame from the access coordinates; and
waiting for a poll packet from the access coordinator to transmit data to the access coordinator.

7. The method of claim 5, further comprising deferring transmission of data for a predetermined time interval.

8. The method of claim 1, further comprising enhancing a time period configured to increase a contention window.

9. The method of claim 8, wherein enhancing a time period configured to increase a contention window comprises allowing a sensor node a predetermined number of attempts to transmit the first data frame.

10. The method of claim 8, further comprising:
initializing the contention window to a predetermined value, wherein the contention window is configured to aid the sensor node in delaying retrying transmission of the first data frame to the access coordinator.

11. A system for communicating data in a wireless control area network, the system comprising:

one or more sensor nodes configured to facilitate acquisition of data; wherein the one or more sensor nodes configured to:

prepare data for transmission from the one or more sensor nodes to an access coordinator in response to a first beacon transmitted from an access coordinator to the one or more sensor nodes, wherein the first beacon is configured to indicate a start of a new communication cycle;

generate a first data frame, wherein the first data frame is indicative of a sensor node having data to transmit, and wherein the first data frame is configured to create a correlation between a poll packet arrival time and a data arrival time at the one or more sensor nodes;

transmit the first data frame from at least one sensor node to an access coordinator;

communicate data from the one or more sensor nodes to an access coordinator in response to the second beacon;

an access coordinator configured to facilitate acquisition of data from the one or more sensor nodes, wherein the access coordinator is configured to:

transmit a first beacon to the one or more sensor nodes, wherein the first beacon is configured indicate a start of a new control cycle;

transmit a second beacon from the access coordinator to a sensor node transmitting the first data frame, wherein the second beacon is configured to:
initiate a polling cycle; and
acknowledge receipt of the first data frame.

12. The system of claim 11, wherein the one or more sensor nodes are further configured to:

verify availability of a transmission channel prior to transmitting the first data frame; and transmit the first data frame from the sensor node to the access coordinator over the available transmission channel.

13. The system of claim 12, wherein the one or more sensor nodes are further configured to defer transmission of the first data frame based on the availability of the transmission channel.

14. The system of claim 13, wherein the one or more sensor nodes are further configured to enhance a time period configured to increase a contention window.

15. The system of claim 11, wherein the access coordinator is further configured to generate a revised polling sequence by moving a sender of the first data frame to the top of a predetermined polling sequence.

16. The system of claim 15, wherein the access coordinator is further configured to poll the one or more sensor nodes as per the revised polling sequence.

17. The system of claim 15, wherein the access coordinator is further configured to transmit a second data frame, wherein the second data frame is indicative of an end of the polling sequence.

18. The system of claim 16, further configured to wirelessly transmit the data from the one or more sensor nodes to the access coordinator.

19. A system for communicating data in a wireless control area network, the system comprising:

one or more sensor nodes configured to facilitate acquisition of data;

wherein the one or more sensor nodes module are configured to:

prepare data for transmission from the one or more sensor nodes to an access coordinator in response to a first beacon transmitted from an access coordinator to the one or more sensor nodes, wherein the first beacon is configured to indicate a start of a new communication cycle;

generate a first data frame, wherein the first data frame is indicative of a sensor node having data to transmit, mad wherein the first data frame is configured to create a correlation between a poll packet arrival time and a data arrival time at the one or more sensor nodes;

transmit the first data frame from at least one sensor node to an access coordinator; and communicate data from the one or more sensor nodes to an access coordinator in response to a second beacon;

an access coordinator configured to facilitate acquisition of data from the one or more sensor nodes, wherein the access coordinator is configured to:

transmit a first beacon to the one or more sensor nodes, wherein the first beacon is configured to indicate a start of a new control cycle;

transmit a second beacon from the access coordinator to the sensor node transmitting the first data frame, wherein the second beacon is configured to:

initiate a polling cycle; and acknowledge receipt of the first data frame.

20. A system for communicating data in a wireless control area network, the system comprising:

an access coordinator configured to facilitate acquisition of data from one or more sensor nodes, wherein the access coordinator is configured to:

transmit a first beacon to one or more sensor nodes, wherein the first beacon is configured indicate a start of a new control cycle;

transmit a second beacon from the access coordinator to a sensor node transmitting a first data frame, wherein the second beacon is configured to:

initiate a polling cycle; and acknowledge receipt of the first data frame;

one or more sensor nodes configured to facilitate acquisition of data;

wherein the one or more sensor nodes are configured to:

prepare data for transmission from the one or more sensor nodes to the access coordinator in response to a first beacon transmitted from an access coordinator to the one or more sensor nodes, wherein the first beacon is configured to indicate a start of a new communication cycle;

generate a first data frame, wherein the first data frame is indicative of a sensor node having data to transmit, and wherein the first data frame is configured to create a correlation between a poll packet arrival time and a data arrival time at the one or more sensor nodes;

transmit the first data frame from at least one sensor node to the access coordinator; and communicate data from the one or more sensor nodes to the access coordinator in response to the second beacon.

21. A computer readable medium comprising one or more non-transitory tangible media, wherein the one or more tangible media comprise:

code adapted to transmit a first beacon from an access coordinator to one or more sensor nodes in a wireless control area network, wherein the first beacon is configured to indicate a start of a new communication cycle;

code adapted to prepare data for transmission from the one or more sensor nodes to the access coordinator in response to the first beacon;

code adapted to generate a first data frame, wherein the first data frame is indicative of a sensor node having data to transmit, and wherein the first data frame is configured to create a correlation between a poll packet arrival time and a data arrival time at the one or more sensor nodes;

code adapted to transmit the first data frame from at least one sensor node to the access coordinator;

code adapted to transmit a second beacon from the access coordinator to the sensor node transmitting the first data frame, wherein the second beacon is configured to initiate polling of data from the one or more sensor nodes; and code adapted to communicate data from the one or more sensor nodes to the access coordinator in response to the second beacon.

* * * * *